US005801227A

United States Patent [19]

Fanslow, III et al.

[11] Patent Number: 5,801,227

[45] Date of Patent: Sep. 1, 1998

[54] ANTIBODIES TO CD40

[76] Inventors: William C. Fanslow, III, 218 SW. 327th Pl., Federal Way, Wash. 98023; JoDee Zappone, 4426—176th St. SW., #J-2, Lynnwood, Wash. 98037; Mark Alderson, 1116 Grow Ave. NW.; Richard J. Armitage, 5133 Eagle Harbor Dr., both of Bainbridge Island, Wash. 98110

[21] Appl. No.: 526,014

[22] Filed: Sep. 8, 1995

Related U.S. Application Data

[63] Continuation of Ser. No. 130,541, Oct. 1, 1993, abandoned.

[51] Int. Cl.$^6$ .................... C07K 16/28; C07K 16/18; C12N 5/12
[52] U.S. Cl. .................... 530/388.73; 530/387.1; 530/387.3; 530/388.1; 530/388.2; 530/388.22; 530/388.7; 530/388.73; 530/389.6; 435/326; 435/328; 435/332; 435/334; 435/343; 435/343.1; 435/346
[58] Field of Search ............... 530/387.1, 387.3, 530/388.1, 388.2, 388.22, 388.7, 388.73, 389.1, 389.6; 435/70.21, 326, 328, 343

[56] References Cited

U.S. PATENT DOCUMENTS 5,247,069  9/1993  Ledbetter ...................... 530/350
5,397,703  3/1995  DeBoer et al.

OTHER PUBLICATIONS

Pen Hartog et al. Immunotechnology 2(4) 299 (1996).
Barrett et al., "CD40 Signaling Activates CD11a/CD18 (LFA–1)–Mediated Adhesion in B Cells," *J. Immunol.* 146:1722, Mar. 1991.
Gordon et al., "Resting B Lymphocytes Can Be Triggered Directly Through The CDw40 (Bp50) Antigen," *J. Immunol.* 140:1425, Mar. 988.
Valle et al., "Activation of human B lymphocytes through CD–40 and interleukin 4," *Eur. J. Immunol.* 19:1463, 1989.
Clark and Ledbetter, "Activation of B human cells mediated through two distinct cell surface differentiation antigens, Bp35 and Bp50," *Proc. Natl. Acad. Sci. USA* 83:4494, Jun. 1986.
Gordon et al, "Two surface antigens, CD23 (p45) and a novel p50 molecule, deliver distinct progression signals to activated B–lymphocytes," A.J. McMichael ed., Oxford University Press, Oxford, p. 426.

Paulie et al., "The Human B Lymphocyte and Carcinoma Antigen, CDw40, Is A Phosphoprotein Involved In Growth Signal Transduction," *J. Immunol.* 142:590, Jan. 1989.
Gordon et al., "Synergistic interaction between interleukin 4 and anti-Bp50 (Cdw40) revealed in a novel B cell restimulation assay," *Eur. J. Immunol.* 17:1535, 1987.
Jabara et al., "CD40 and IgE: Synergism between Anti–CD40 Monoclonal Antibody and Interleukin 4 in the Induction of IgE Synthesis by Highly Purified Human B Cells," *J. Exp. Med.* 172:1861, Dec. 1990.
Gascan et al., "Anti–CD40 Monoclonal Antibodies Or CD$^+$ Cell Clones and IL–4 Induce IgG4 And IgE Switching In Purified Human B Cells Via Different Signaling Pathways," *J. Immunol.* 147:8, Jul. 1991.
Gordon and Guy, "The molecules controlling B lymphocytes," *Immunol. Today* 8:339, 1987.
Cairns et al., "Soluble CD23 is released by B lymphocytes cycling in response to interleukin 4 and anti–Bp50 (CDw40)" *Eur. J. Immunol.* 18:349, 1988.
Clark and Shu, "Association Between IL–6 and CD40 Signaling IL–6 Induces Phosphorylation of CD40 Receptors," *J. Immunol.* 145:1400, Sep. 1990.
Banchereau et al., "Long Term Human B Cell Lines Dependent on Interleukin–4 and Antibody to CD40," *Science* 241:70, Jan. 1991.
Liu et al, "Mechanism of antigen–driven selection in germinal centres," *Nature* 342:929, Dec. 1989.
Howard et al., Abstract "Antibodies to Murine CD40 Stimulate Normal B Cells But Inhibit Proliferation of B Lymphoma Cells," from Keystone Meetings, Jan./Feb. 1993.
Fanslow et al, Soluble Forms of CD40 Inhibit Biologic Responses of Human B Cells, *J. Immunol.* 149:655, Jul. 1992.
Rousset et al., "Cytokine–induced Proliferation and Immunoglobulin Production of Human B Lymphocytes Triggered through Their CD40 Antigen," *J. Exp. Med.* 173:705, Mar. 1991.
Splawski et al., "Immunoregulatory Role of CD40 in Human B Cell Differentiation," *J. Immunol.* 150:1276, Feb. 1993.
Dorken et al. Leucocyte Typing IV Knapp et al. 90–91 (1992).
Harris et al. TIBTECH 11:42–44 (1993).
I. Kwekkeboom et al. Immunology 79:439–444 (1993).

*Primary Examiner*—Lila Feisee
*Assistant Examiner*—Phillip Gambel
*Attorney, Agent, or Firm*—Patricia Anne Perkins

[57] ABSTRACT

The present invention provides monoclonal antibodies and binding proteins which specifically bind to CD40 and are capable of blocking binding of CD40 to CD40 ligand.

6 Claims, 4 Drawing Sheets

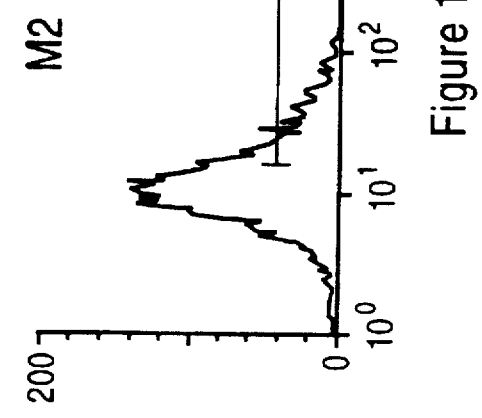
Figure 1A Control
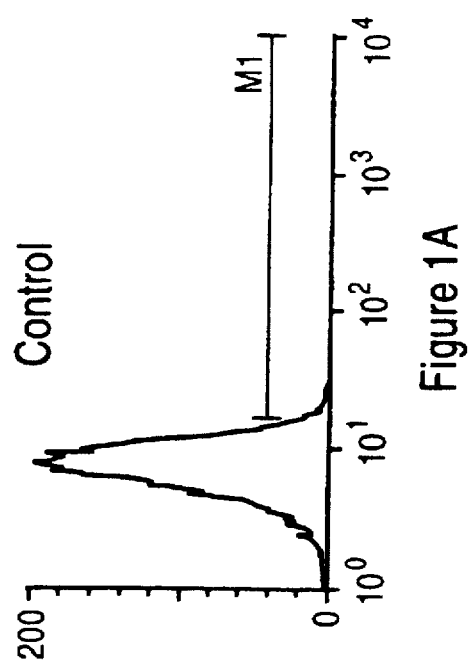
Figure 1B msIgG
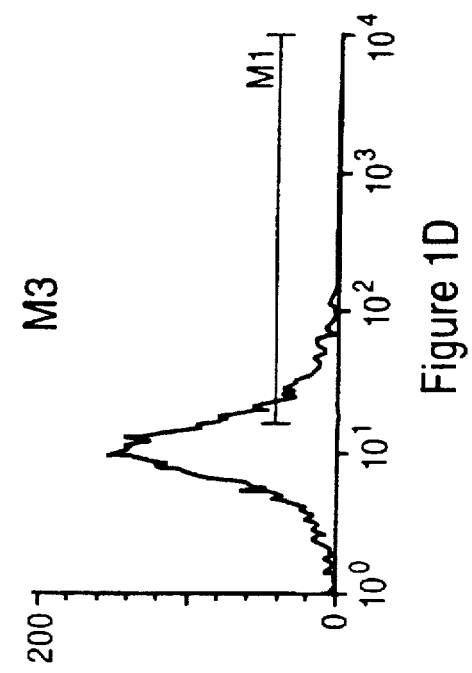
Figure 1C M2
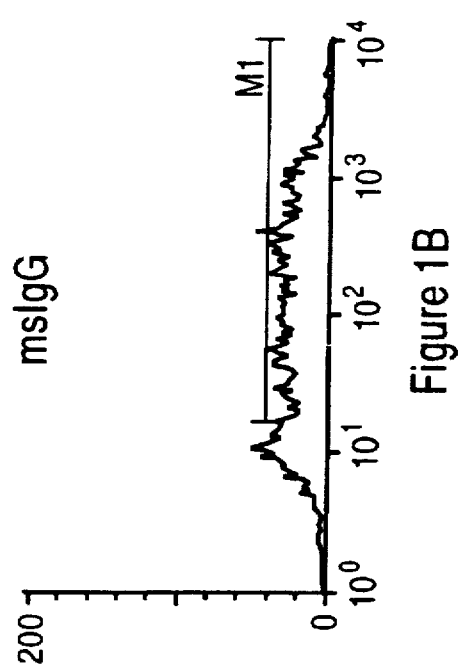
Figure 1D M3

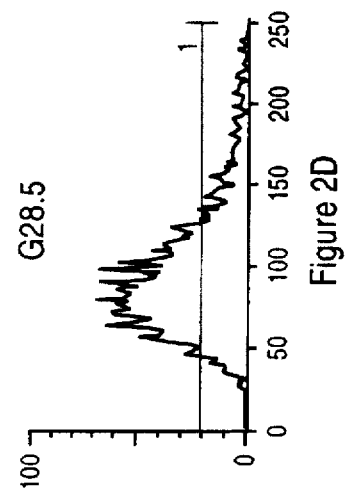
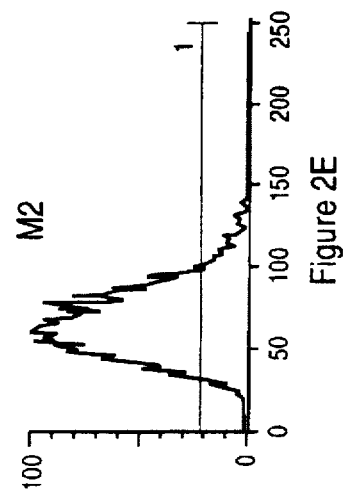
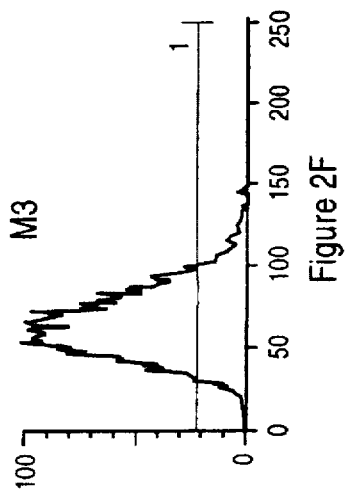
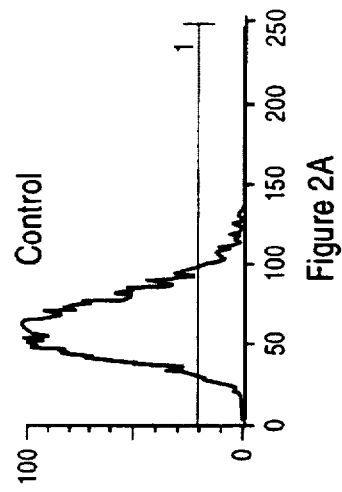
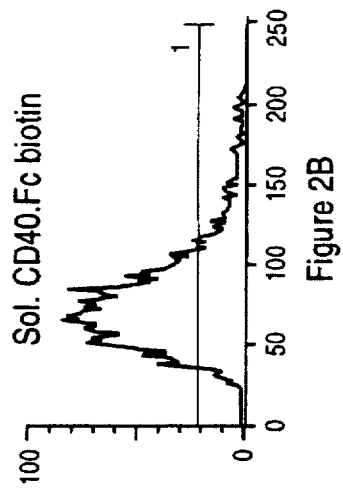
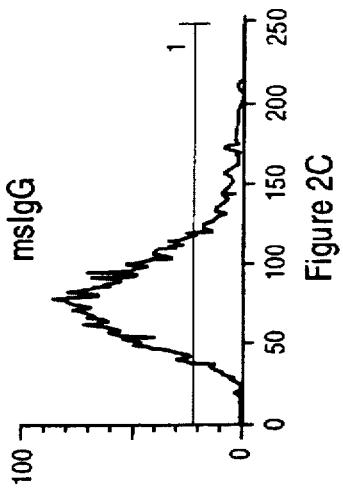

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Asp Tyr Lys Asp Asp Asp Asp Lys
    1                5

ANTIBODIES TO CD40

This is a continuation of U.S. application Ser. No. 08/130,541, filed Oct. 1, 1993, now abandoned.

TECHNICAL FIELD

The present invention relates generally to antibodies and, more specifically, to antibodies against CD40.

BACKGROUND OF THE INVENTION

CD40 is a 50 kDa surface antigen expressed on B cells, dendritic cells, some carcinoma cell lines and human thymic epithelium. CD40 is known to play an important role in the proliferation and differentiation of B lymphocytes. Based on similarities of amino acid sequence, CD40 has been identified as a member of the TNF receptor family of proteins, which includes such molecules as the low affinity receptor for nerve growth factor, both forms of TNF receptors, CD27, OX40, and the Hodgkin's lymphoma marker CD30. Both human and murine forms of a ligand for CD40 (CD40L) were recently cloned and demonstrated to be type II integral membrane proteins expressed primarily on activated CD4+ T cells. CD40L provides a strong stimulatory signal to B cells from both human and murine species; however, little is known about the regulation of expression of CD40L and the effects of CD40L on other cell types.

Monoclonal antibodies directed against the CD40 surface antigen have also been shown to mediate various biological activities on human B cells. For example, CD40 mAb induce homotypic and heterotypic adhesions (Barrett et al., *J. Immunol.* 146:1722, 1991; Gordon et al., *J. Immunol.* 140:1425, 1988), and increase cell size (Gordon et al., *J. Immunol.* 140:1425, 1988; Valle et al., *Eur. J. Immunol.* 19:1463, 1989). CD40 induce proliferation of B cells activated with anti-IgM, CD20 mAb, or phorbol ester alone (Clark and Ledbetter, *Proc. Natl. Acad. Sci. U.S.A.* 83:4494, 1986; Gordon et al., LEUCOCYTE TYPING III. A. J. McMichael ed. Oxford University Press. Oxford, p. 426; Paulie et al., *J. Immunol.* 142:590, 1989) or in concert with IL-4 (Valle et al., *Eur. J. Immunol.* 19:1463, 1989; Gordon et al., *Eur. J. Immunol.* 17:1535, 1987), and produce IgE (Jabara et al., *J. Exp. Med.* 172:1861, 1990; Gascan et al., *J. Immunol.* 147:8, 1991), IgG, and IgM (Gascan et al., *J. Immunol.* 147:8, 1991) from IL-4-stimulated T cell-depleted cultures. In addition, CD40 mAb have been reported to enhance IL-4-mediated soluble CD23/FcεRII release from B cells (Gordon and Guy, *Immunol. Today* 8:339, 1987; Cairns et al., *Eur. J. Immunol.* 18:349, 1988) and to promote B cell production of IL-6 (Clark and Shu, *J. Immunol.* 145:1400, 1990). Recently, in the presence of $CD_w32+$ adherent cells, human B cell lines have been generated from primary B cell populations with IL-4 and CD40 mAb (Banchereau et al., *Science* 241:70, 1991). Furthermore, germinal center centrocytes can be prevented from undergoing apoptosis if they are activated through CD40 and/or receptors for Ag (Liu et al., *Nature* 342:929, 1989). Each of the above publications describes CD40 mAb that stimulate a biological activity of B cells.

Monoclonal antibodies that block binding of CD40 to CD40 ligand, however, have not yet been disclosed. Such blocking antibodies would be useful, for example, in research applications to further elucidate the role of CD40 and also in therapeutic applications requiring inhibition CD40 mediated biological activity. CD40 blocking mAbs would also be useful in clinical applications, for example, for diagnosis of CD40 associated diseases. Additionally, antibodies may be utilized in various research applications such as the purification of recombinantly produced CD40, or in assays which detect the presence of the CD40.

The present invention provides such antibodies and, furthermore, provides other related advantages.

SUMMARY OF THE INVENTION

The present invention provides monoclonal antibodies which specifically bind to a human CD40 molecule and block binding of the CD40 molecule to a CD40 ligand. The monoclonal antibody may be selected from the group consisting of human and mouse monoclonal antibodies. Similarly, the CD40 may be selected from the group consisting of murine and human CD40. A therapeutic composition is also provided comprising a monoclonal antibody to the CD40 as described above and a physiologically acceptable carrier or diluent.

The invention also provides a binding protein which specifically binds to a mammalian CD40, which may be, for example, a fragment of an antibody or a fusion protein comprising at least one domain derived from an antibody. A therapeutic composition is also provided comprising a binding protein which specifically binds to mammalian CD40, and a physiologically acceptable carrier or diluent.

The present invention also includes a method for detecting CD40 on cells, comprising the steps of (a) incubating the cells with a monoclonal antibody, as described above, which is labeled, and (b) detecting the presence of bound antibody. The invention also provides a method for detecting soluble CD40 in serum comprising the steps of (a) incubating serum suspected of containing soluble CD40 with a solid support having monoclonal antibodies as described above affixed thereto under conditions and for a time sufficient for binding to occur, (b) incubating the solid support with a second labeled monoclonal antibody specific for CD40 under conditions and for a time sufficient for binding to occur, and (c) detecting the presence of bound labeled antibody.

These and other aspects of the present invention will become evident upon reference to the following detailed description and attached drawings.

BRIEF DESCRIPTION OF THE DRAWINGS

FIG. 1 shows inhibition of soluble human CD40 binding to human CD40L by HuCD40-M2 and HuCD40-M3.

FIG. 2 shows inhibition of soluble human CD40 binding to murine CD40L by HuCD40-M2 and HuCD40-M3.

DETAILED DESCRIPTION OF THE INVENTION

Figure 3:
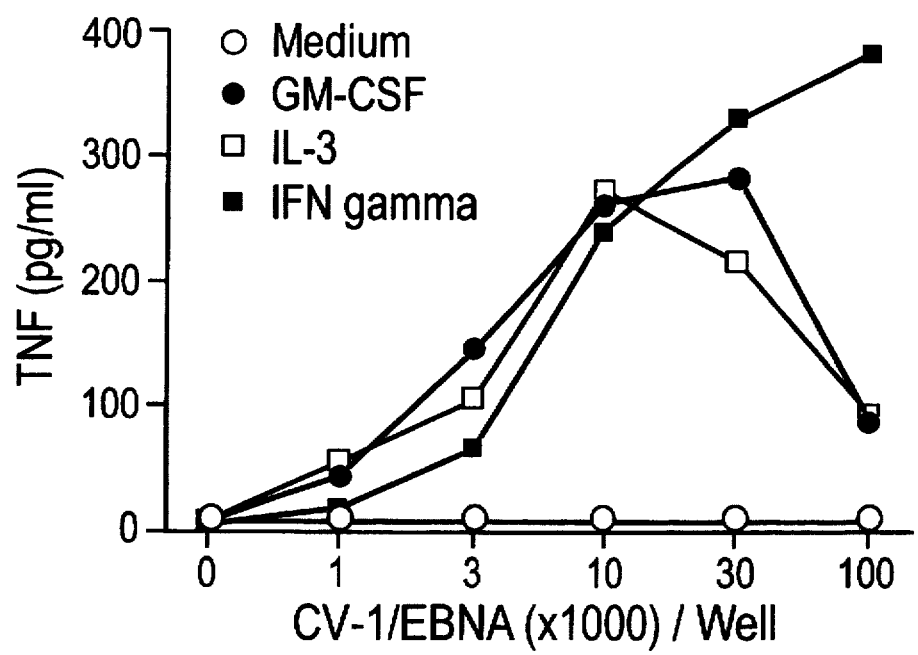
FIG. 3 is a graph showing a dose-dependent relationship between CD40L (expressed on the surface of CV-1/EBNA cells) and TNF-α production of monocytes in the presence of GM-CSF, IL-3 or IFN-γ.

Purified CD40 may be utilized to prepare monoclonal antibodies, as well as other binding proteins which may be specifically constructed utilizing recombinant DNA methods. These binding proteins incorporate the variable regions from a gene which encodes a specifically binding monoclonal antibody. In the context of the present invention, monoclonal antibodies and binding proteins are defined to be specifically binding if they bind with a $K_a$ of greater than or equal to $10^7$ $M^{-1}$. In preferred aspects of the invention, the monoclonal antibodies will also block binding of CD40 to the CD40 ligand (CD40L). The affinity of a monoclonal antibody or binding protein may be readily determined by one of ordinary skill in the art (see Dower et al., "The Interaction of Monoclonal Antibodies with MHC Class I Antigens on Mouse Spleen Cells. I. Analysis of the Mechanism of Binding," *J. Immunol.* 132:751, 1984). Briefly, increasing amounts of radiolabeled antibody or binding protein are exposed to CD40. An antibody's affinity may be determined by taking the reciprocal of the antibody concentration at which one-half of the antibodies maximally bind (see Dower et al., supra). As will be evident to one of ordinary skill in the art, antibodies may be generated against cells bearing CD40, whole CD40, or portions of CD40. Particularly preferred are antibodies developed against CD40 using a soluble CD40.Fc molecule. Additionally, within the context of the present invention monoclonal antibodies include $F(ab')_2$ and Fab fragments which may be readily prepared by one of ordinary skill in the art.

Polyclonal antibodies may be readily generated by one of ordinary skill in the art from a variety of warm-blooded animals such as horses, cows, various fowl, rabbits, mice, or rats. Briefly, CD40 is utilized to immunize the animal through intraperitoneal, intramuscular, intraocular, or subcutaneous injections. The immunogenicity of CD40 may be increased through the use of an adjuvant such as Freund's complete or incomplete adjuvant. Following several booster immunizations, small samples of serum are collected and tested for reactivity to CD40 by any of a number of methods, including among others, assays such as an ELISA, ABC or modified ABC assays, or by a dot blot assay. Particularly preferred polyclonal antisera will give a signal on one of these assays that is at least three times greater than background. Once the titer of the animal has reached a plateau in terms of its reactivity to the CD40, larger quantities of polyclonal antisera may be readily obtained either by weekly bleedings, or by exsanguinating the animal.

Monoclonal antibodies may also be readily generated using conventional techniques (see U.S. Pat. Nos. Re. 32,011, 4,902,614, 4,543,439, and 4,411,993 which are incorporated herein by reference; see also *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), Cold Spring Harbor Laboratory Press, 1988, which are also incorporated herein by reference). Briefly, in one embodiment a subject animal such as a rat or mouse is injected with a form of CD40 suitable for generating an immune response against the CD40. This may be accomplished by immunization with various forms of CD40, including among others, cells which express the CD40, viruses such as the vaccinia virus which express the CD40, soluble forms of the CD40, such as CD40.Fc, or peptides which are based upon the CD40 sequence. Additionally, many techniques are known in the art for increasing the resultant immune response, for example by coupling the soluble receptor or peptide to another protein such as ovalbumin or keyhole limpet hemocyanin (KLH), or through the use of adjuvants such as Freund's complete or incomplete adjuvant. The initial immunization may be through intraperitoneal, intramuscular, intraocular, or subcutaneous routes.

Between one and three weeks after the initial immunization the animal may be reimmunized with another booster immunization. The animal may then be test bled and the serum tested for immunoreactivity to the CD40 using assays such as an ELISA, dot blot, ABC or modified ABC assay. Additional immunizations may also be accomplished until the animal has plateaued in its reactivity to the CD40. The animal may then be given a final boost of soluble CD40, and three to four days later sacrificed. At this time, organs which contain large numbers of B cells such as the spleen and lymph nodes may be harvested and disrupted into a single cell suspension by passing the organs through a mesh screen or by rupturing the spleen or lymph node membranes which encapsidate the cells. Within one embodiment the red cells are subsequently lysed by the addition of a hypotonic solution, followed by immediate return to isotonicity.

In another embodiment, suitable cells for preparing monoclonal antibodies are obtained through the use of in vitro immunization techniques. Briefly, an animal is sacrificed and the spleen and lymph node cells are removed as described above. A single cell suspension is prepared, and the cells are placed into a culture which contains a form of the CD40, which is suitable for generating an immune response as described above. Subsequently, the lymphocytes are harvested and fused as described below.

Cells which are obtained through the use of in vitro immunization or from an immunized animal as described above may be immortalized by transfection with a virus such as the Epstein bar virus (EBV) (see Glasky and Reading, *Hybridoma* 8(4):377–389, 1989). Alternatively, within a preferred embodiment, the harvested spleen and/or lymph node cell suspensions are fused with a suitable myeloma cell in order to create a "hybridoma" which secretes monoclonal antibody. Suitable myeloma lines are preferably defective in the construction or expression of antibodies, and are additionally syngeneic with the cells from the immunized animal. Many such myeloma cell lines are well known in the art and may be obtained from sources such as the American Type Culture Collection (ATCC), Rockville, Md. (see *Catalogue of Cell Lines & Hybridomas*, 6th ed., ATCC, 1988). Representative myeloma lines include: for humans UC 729-6 (ATCC No. CRL 8061), MC/CAR-Z2 (ATCC No. CRL 8147), and SKO-007 (ATCC No. CRL 8033); for mice SP2/0-AG14 (ATCC No. CRL 1581), and P3X63Ag8 (ATCC No. TIB 9), and for rats Y3-Ag1.2.3 (ATCC No. CRL 1631), and YB2/0 (ATCC No. CRL 1662). Particularly preferred fusion lines include NS-1 (ATCC No. TIB 18), and P3X63 - Ag 8.653 (ATCC No. CRL 1580) which may be utilized for fusions with either mouse, rat, or human cell lines. Fusion between the myeloma cell line and the cells from the immunized animal may be accomplished by a variety of methods, including the use of polyethylene glycol (PEG) (see *Antibodies: A Laboratory Manual*, Harlow and Lane (eds.), Cold Spring Harbor Laboratory Press, 1988) or electrofusion (see Zimmerman and Vienken, *J. Membrane Biol.* 67:165–182, 1982).

Following the fusion, the cells may be placed into culture plates containing a suitable medium, such as RPMI 1640, or DMEM (Dulbecco's Modified Eagles Medium) (JRH Biosciences, Lenexa, Kans.). The medium may also contain additional ingredients, such as Fetal Bovine Serum (FBS, i.e., from Hyclone, Logan, Utah, or JRH Biosciences), thymocytes which were harvested from a baby animal of the same species as was used for immunization, or agar to solidify the medium. Additionally, the medium should contain a reagent which selectively allows for the growth of fused spleen and myeloma cells. Particularly preferred is the use of HAT (hypoxanthine, aminopterin, and thymidine) (Sigma Chemical Co., St. Louis, Mo.). After about seven days, the resulting fused cells or hybridomas may be screened in order to determine the presence of antibodies which recognize CD40. Following several clonal dilutions and reassays, a hybridoma producing antibodies which bind to CD40 may be isolated.

Other techniques may also be utilized to construct monoclonal antibodies (see William D. Huse et al., "Generation of a Large Combinational Library of the Immunoglobulin Repertoire in Phage Lambda," *Science* 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. U.S.A.* 86:5728–5732, August 1989; see also Michelle Alting-Mees et al., "Monoclonal Antibody Expression Libraries: A Rapid Alternative to Hybridomas," *Strategies in Molecular Biology* 3:1–9, January 1990; these references describe a commercial system available from Stratacyte, La Jolla, Calif., which enables the production of antibodies through recombinant techniques). Briefly, mRNA is isolated from a B cell population, and utilized to create heavy and light chain immunoglobulin cDNA expression libraries in the kImmunoZap(H) and kImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid which allows high level expression of monoclonal antibody fragments from *E. coli*.

Similarly, binding proteins may also be constructed utilizing recombinant DNA techniques to incorporate the variable regions of a gene which encodes a specifically binding antibody that blocks binding of CD40 to CD40L. The construction of these proteins may be readily accomplished by one of ordinary skill in the art (see James W. Larrick et al., "Polymerase Chain Reaction Using Mixed Primers: Cloning of Human Monoclonal Antibody Variable Region Genes From Single Hybridoma Cells," *Biotechnology* 7:934–938, September 1989; Riechmann et al., "Reshaping Human Antibodies for Therapy," *Nature* 332:323–327, 1988; Roberts et al., "Generation of an Antibody with Enhanced Affinity and Specificity for its Antigen by Protein Engineering," *Nature* 328:731–734, 1987; Verhoeyen et al., "Reshaping Human Antibodies: Grafting an Antilysozyme Activity," *Science* 239:1534–1536, 1988; Chaudhary et al., "A Recombinant Immunotoxin Consisting of Two Antibody Variable Domains Fused to Pseudomonas Exotoxin," *Nature* 339:394–397, 1989), given the disclosure provided herein. Briefly, the antigen-binding sites or CD40 binding domain from a cell which produces a specifically binding and blocking monoclonal antibody are amplified, and inserted directly into the genome of a cell which produces human antibodies (see Verhoeyen et al., supra; see also Reichmann et al., supra). This technique allows the antigen-binding site of a specifically binding murine or rat monoclonal antibody to be transferred into a human antibody. Such antibodies are preferable for therapeutic use in humans because they are not as antigenic as rat or mouse antibodies. Alternatively, the antigen-binding sites (variable region) may be either linked to, or inserted into, another completely different protein (see Chaudhary et al., supra), resulting in a new protein with antigen-binding sites of the antibody as well as the functional activity of the completely different protein. As one of ordinary skill in the art will recognize, the antigen-binding sites or CD40 binding domain of the antibody may be found in the variable region of the antibody. Furthermore, DNA sequences which encode smaller portions of the antibody or variable regions which specifically bind to mammalian CD40 may also be utilized within the context of the present invention. These portions may be readily tested for binding specificity to the CD40 utilizing assays known in the art, including for example ELISA, ABC, or dot blot assays.

In a preferred embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Stratacyte (La Jolla, Calif.) sells primers for mouse and human variable regions including, among others, primers for $V_{Ha}$, $V_{Hb}$, $V_{Hc}$, $V_{Hd}$, $C_{H1}$, $V_L$ regions. These primers may be utilized to amplify heavy or light chain variable regions, which may then be inserted into vectors such as ImmunoZAP* H or ImmunoZAP* L (Stratacyte), respectively. These vectors may then be introduced into *E. coli* for expression. Utilizing these techniques, large amounts of a single-chain protein containing a fusion of the $V_H$ and $V_L$ domains may be produced (see Bird et al., *Science* 242:423–426, 1988).

In another embodiment, the binding protein is fused within the expression vector to another protein, such as a toxin. Cells which are bound by the binding protein may thus be killed by incorporation of the toxin (see Chaudhary et al.). Alternatively, the binding protein may be fused to an CD40L antagonist (i.e., a protein which binds CD40 but generates no biological activity), allowing large local concentrations of the antagonist to be developed around cells which express CD40. Only cells which could bind the antagonist would be affected, potentially decreasing the dose needed for therapeutic purposes.

Once suitable antibodies or binding proteins have been obtained, they may be isolated or purified by many techniques well known to those of ordinary skill in the art (see *Antibodies: A Laboratory Manual*, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

Antibodies and binding proteins of the present invention have many uses. For example, antibodies may be utilized in flow cytometry to sort CD40 bearing cells, or to histochemically stain CD40 bearing cells. Briefly, in order to detect CD40 on cells, the cells are incubated with a labeled monoclonal antibody which specifically binds to mammalian CD40, followed by detection of the presence of bound antibody. These steps may also be accomplished with additional steps such as washings to remove unbound antibody. Labels suitable for use within the present invention are well known in the art including, among others, Flourescein Isothiocyanate (FITC), Phycoerythrin (PE), Horse Radish Peroxidase (HRP), and colloidal gold. Particularly preferred for use in flow cytometry is FITC which may be conjugated to purified antibody according to the method of Keltkamp in "Conjugation of Fluorescein Isothiocyanate to Antibodies. I. Experiments on the Conditions of Conjugation," *Immunology* 18:865–873, 1970. (See also Keltkamp, "Conjugation of Fluorescein Isothiocyanate to Antibodies. II. A Reproducible Method," *Immunology* 18:875–881, 1970; and Goding, "Conjugation of Antibodies with Fluorochromes: Modification to the Standard Methods," *J. Immunol. Methods* 13:215–226, 1970.) For histochemical staining, HRP is preferred, which may be conjugated to the purified antibody according to the method of Nakane and Kawaoi in "Peroxidase-Labeled Antibody: A New Method of Conjugation," *J. Histochem. Cytochem.* 22:1084–1091, 1974. (See also Tijssen and Kurstak, "Highly Efficient and Simple Methods for Preparation of Peroxidase and Active Peroxidase Antibody Conjugates for Enzyme Immunoassays," *Anal. Biochem.* 136:451–457, 1984.)

Purified antibodies or binding proteins may also be utilized therapeutically to block the binding of CD40-L to CD40 in vivo, or for in vivo neutralization of CD40 bearing cells. In preferred embodiments, the antibody is modified to escape immunological detection, for example, by transferring the antigen-binding site of a specific murine monoclonal antibody to a human monoclonal antibody, as discussed above. Particularly preferred is the use of therapeutic compositions comprising an antibody or binding protein to CD40, and a physiologically acceptable carrier or diluent. Suitable carriers or diluents include, among others, neutral buffered saline or saline mixed with nonspecific albumin. Additionally, the therapeutic composition may include further excipients or stabilizers such as buffers, carbohydrates including, for example, glucose, sucrose, or dextrose, chelating agents such as EDTA, or various preservatives. Appropriate dosages may be determined in clinical trials, although the amount and frequency of administration may be dependent on such factors as the nature and severity of the indication being treated, the desired response, and the condition of the patient.

Antibodies may also be utilized to monitor the presence of circulating soluble CD40 which has been administered to a patient, or to measure in vivo levels of CD40 in patients. Within a preferred embodiment, a double determinant or sandwich assay is utilized to detect the CD40. Briefly, serum suspected of containing soluble CD40 is incubated with a solid support having a monoclonal antibody, as described above, affixed thereto under conditions and for a time sufficient for binding to occur. Many solid supports are known in the art, including, among others, ELISA plates (Linbro, McLean, Va.), nitrocellulose (Millipore Corp. Bedford, Mass.), beads (Polysciences, Warrington, Pa.), and magnetic beads (Robbin Scientific, Mountain View, Calif.). Additionally, the monoclonal antibody may be readily affixed to the solid support utilizing techniques well known in the art (see *Antibodies: A Laboratory Manual*, Harlow and Lane (eds.), Cold Spring Harbor Laboratory Press, 1988). The solid support is then incubated with a second labeled monoclonal antibody specific for mammalian CD40 under conditions and for a time sufficient for binding to occur, after which presence of bound labeled antibody may be detected.

Within a particularly preferred embodiment, a monoclonal antibody is coated onto a solid support such as a 96 well plate. Subsequently, the plate is blocked with a protein such as bovine serum albumin or nonfat dry milk for about 30 minutes. Serum from a patient is diluted in phosphate buffered saline and incubated in the wells under conditions and for a time sufficient for binding to occur, generally about 30 minutes. Subsequently, the plate is washed and a labeled second monoclonal antibody specific for a different CD40 epitope is added into the wells and incubated as described above. Antibodies for different CD40 may be determined through the use of cross-blocking assays. The well is then examined for the presence of the second labeled antibody. Presence of the second labeled antibody indicates the presence of the CD40 in the patient's serum. As will be understood by one of ordinary skill in the art, the monoclonal antibodies used in the above assay may be substituted with polyclonal antibodies or binding proteins which are specific for CD40.

The following examples are offered by way of illustration, and not by way of limitation.

EXAMPLES

Example I

Preparation of Monoclonal Antibodies to CD40

Monoclonal antibodies that bind to human CD40 and block binding of CD40 to CD40 ligand were generated as follows. A human CD40 immunogen, consisting of the extracellular domain of CD40 fused to a human IgG1 Fc molecule (referred to as HuCD40.Fc), was prepared substantially as described by Fanslow et al., *J. Immunol.* 149:655, 1992.

BALB/C mice were injected with 10 µg of huCD40.Fc, both intraperitoneally and subcutaneously, and emulsified with complete Freunds adjuvant. Thirteen and nineteen days later the mice were injected subcutaneously with 10 µg of huCD40.Fc (emulsified with incomplete Freunds adjuvant). Sera samples were collected after 6 days later by retro-orbital bleeding. Sera samples were tested by dot blot, antibody capture plate assay and FACS anaylysis (using either membrane bound huCD40 or soluble Flag HuCD40. Flag HuCD40 has an N-terminal "flag" peptide Asp-Tyr-Lys-Asp-Asp-Asp-Asp-Lys (SEQ ID NO) (Hopp et al., *Bio/Technology* 6:1204,1988) that is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys pairing. Sera samples had titers of >1:2100 in a dot blot assay (using 25 µg Flag huCD40 per dot), and approximately 1:1600 in an antibody capture format ELISA assay (using biotin-labelled Flag huCD40 at 150 ng/ml) and >1: 1600 in an antibody capture plate assay (using $I^{125}$-labelled Flag huCD40 at 3000 cpm/µl). Sera was also tested in FACS assay at a 1:400 dilution using cells which express huCD40 on their cell surface, and found to show a mean fluorescence shift of 4 times greater than normal mouse sera.

Mice were rested for about 8 weeks and immunized with 7 µg huCD40.Fc subcutaneously (emulsified with incomplete Freunds adjuvent). Four and a half weeks later one mouse was given 2 µg huCD40.Fc intravenously without adjuvent. Three days later that mouse was sacrificed. Spleen cells were then harvested and fused to a murine myeloma cell line (Ag 8.653). The fusion was plated in 96 well plates in HAT selective medium (hypoxanthine, aminopterin, and thymidine) to inhibit proliferation of non-fused cells, myeloma hybrids, and spleen cell hybrids.

Hybridoma cell supernatants were screened by two assays. Both assays were performed in 96-well plates coated with 10 µg/ml Goat anti-mouse antibody. Briefly, the positive screen, for huCD40.Fc reactivity was performed as follows. Coated and blocked plates were washed, and primary antibody (hybridoma cell supernatants) were added and incubated. Plates were washed again, and biotin labelled huCD40.Fc was added and incubated. Plates were washed again, and streptavidin HRP (horseradish peroxidase conjugate) was added and incubated. As a final step, plates were washed, and TMB (3,3', 5,5'-tetramethyl-benzidine) peroxidase substrate was added. Color was allowed to develop and was read out using an ELISA plate reader.

The negative screen for Fc reactivity was performed as follows. Coated and blocked plates were washed, and primary antibody (hybridoma cell supernatants) were added and incubated. Plates were washed again, and huIgG1 HRP (horseradish peroxidase conjugate) was added and incubated. As a final step, plates were washed, and TMB peroxidase substrate was added. Color was allowed to develop and was read out using an ELISA plate reader.

As secondary screens hybridoma supernatants were also tested for their ability to block binding of biotin labelled huCD40.Fc to cells expressing huCD40 ligand on their cell surface using FACS analysis and against biotin labelled Flag huCD40 in the same assay format as the primary (positive) screen.

Utilizing the above methods, two distinct hybridoma clones were isolated which bind CD40 and block binding of CD40 to CD40L. These two clones are referred to as HuCD40-M2 (M2) and HuCD40-M3 (M3). The hybridoma clone HuCD40-M2 generated according to the above procedure has been deposited with the American Type Culture Collection, 12301 Parklawn Drive, Rockville, Md. 20852, U.S.A. (Accession No. HB 11459) on Oct. 6, 1993, under the conditions of the Budapest Treaty.

Hybridoma clones can be screened by ELISA for reactivity with CD40, for example, by adaptations of the techniques disclosed by Engvall et al., Immunochemistry 8:871, 1971, and in U.S. Pat. No. 4,703,004. Positive clones are then injected into the peritoneal cavities of syngeneic BALB/C mice to produce ascites containing high concentrations (>1 mg/ml) of anti-CD40 monoclonal antibody. The resulting monoclonal antibody can be purified by ammonium sulfate precipitation followed by gel exclusion chromatography, and/or affinity chromatography based on binding of antibody to Protein A of Staphylococcus aureus.

Example 2

Inhibition of CD40 Binding to CD40L

HuCD40-M2 and HuCD40-M3 were shown to inhibit binding of huCD40.Fc to huCD40L as follows. Purified human peripheral blood T cells were stimulated for 18 hrs with PMA and ionomycin to induce human CD40L expression. The T cells were then bound with human IL-4R.Fc (5 µg/ml) as a negative control protein or with huCD40.Fc (5 µg/ml) and binding inhibition performed with irrelevant ms IgG (20 µg/ml), with HuCD40-M2 (20 µg/ml) or with HuCD40-M3 (20 µg/ml). The bound CD40.Fc was detected by flow cytometric analysis with an anti human Fc Ab-biotin and streptavidin-phycoerythrin. As shown in FIG. 1, at these concentrations both HuCD40-M2 and HuCD40-M3 inhibited CD40.Fc binding by >90% as compared to irrelevant ms IgG.

HuCD40-M2 and HuCD40-M3 were shown to inhibit binding of huCD40.Fc to HuCD40 as follows. HL40.9 cells that constituitively express HuCD40L were bound with control protein or with a sub-optimal concentration of huCD40.Fc biotin (2.5 µg/ml) and binding inhibition performed with irrelevant ms IgG (50 µg/ml), a control ms IgG1 mAb G28.5 (50 µg/ml) (provided by Dr. Edward A. Clark, University of Washington), with HuCD40-M2 (12.5 µg/ml) or with HuCD40-M3 (12.5 µg/ml). The bound biotin-labeled CD40.Fc was detected by flow cytometric analysis using streptavidin-phycoerythrin. As shown in FIG. 2, at these concentrations both HuCD40-M2 and HuCD40-M3 inhibited CD40.Fc binding by >95% as compared to irrelevant ms IgG or ms IgG1 mAb G28.5.

Example 3

Inhibition of Biological Activity of CD40 Using CD40 MAB

This example shows that HuCD40-M2 blocks CD40 biological activity by inhibiting CD40L mediated TNF-a production. Monocyte cultures were established by first purifying monocytes from normal donor PBMC by countercurrent elutriation as described by Alderson et al., J. Exp. Med. 173:923, 1991, and were at least 95% pure by microscopic examination of Giemsa-stained cytocentrifuge preparations. Cells were cultured in RPMI1640 medium containing 10% low endotoxin FBS, 50 U/ml penicillin, 50 mg/µl streptomycin and $5 \times 10^{-5}$ M 2-mercaptoethanol.

The following reagents were prepared. CV-1/EBNA cells expressing CD40L were fixed with paraformaldehyde 2 days after transfection, as described by Armitage et al., Nature (Lond.) 357:80, 1992 and Spriggs et al., J. Exp. Med. 176:1543, 1992. Recombinant IL-3, IL-4 and GM-CSF were purified as described by Alderson et al., J. Immunol. 149:1252, 1992, and had specific activities of $9 \times 10^4$, $1 \times 10^4$ and $5 \times 10^4$ U/µg. The CD40 molecule used was a soluble CD40 fusion protein consisting of the extracellular domain of CD40 coupled to the Fc region of human IgG1, constructed and purified as described above in Example 1.

Monocytes cultures were established in 24-well plates (Costar, Cambridge, Mass.), together with increasing numbers of CV-1/EBNA cells transiently expressing CD40L either alone or in the presence of GM-CSF, IL-3 or IFN-γ (10 ng/ml). TNF-α levels were detected at 24 hours by ELISA. FIG. 3 shows a dose-dependent relationship between CD40L induction and TNF-α production. As few as $10^3$ CV-1/EBNA cells expressing CD40L were sufficient to induce TNF-α production in the presence of GM-CSF, IL-3 or IFN-γ, yet even large numbers of these cells alone were unable to induce significant TNF-α production.

Figure 4:
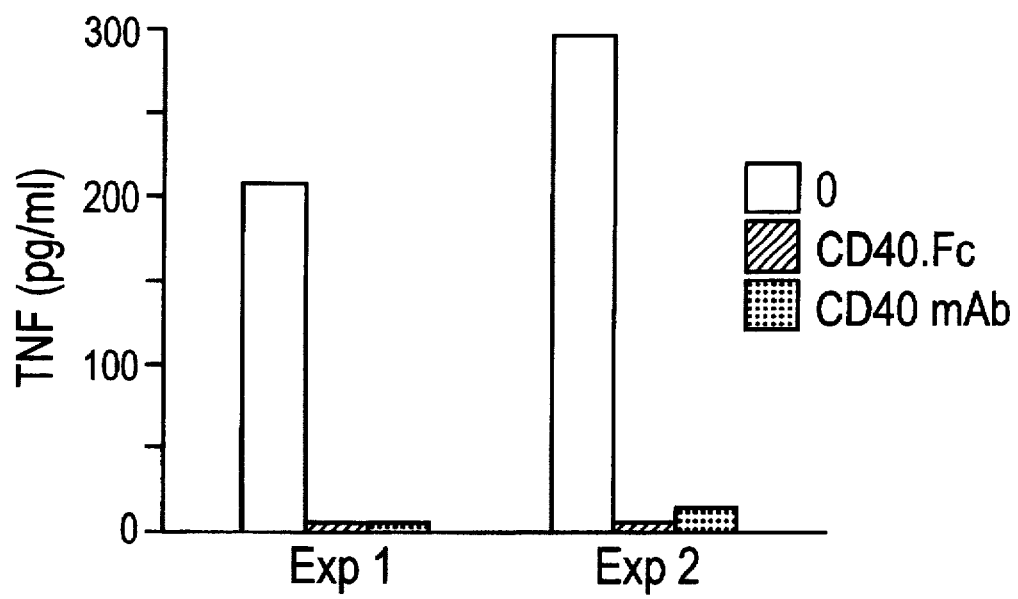
FIG. 4 is a graph showing that CD40L induced TNF-α production of monocytes is inhibited by CD40.Fc or HuCD40-M2.

CD40.Fc or HuCD40-M2 were both shown to be able to inhibit CD40L-induced TNF-α production. Monocytes were stimulated with CD40L in the presence of GM-CSF. CD40.Fc and HuCD40-M2 were used at a final concentration of 10 µg/ml. TNF-α was non-detectable (<5 µg/ml) in control cultures with medium alone, GM-CSF alone, CD40L alone, CD40.Fc alone or CD40 antibody alone. FIG. 4 shows that in the absence of either CD40.Fc or HuCD40-M2, TNF-a production is stimulated with CD40L in the presence of GM-CSF. In contrast, both CD40.Fc and the CD40 blocking HuCD40-M2 inhibited TNF-α production induced by CD40L in the presence of GM-CSF. An isotype control mAb and human IgG1 were unable to block TNF-a production in this assay (data not shown). These data indicate that HuCD40-M2 specifically binds to a human CD40 molecule and is capable of blocking binding of the CD40 molecule to a CD40 ligand. These data further suggest that the HuCD40-M2 may be useful in blocking TNF-α mediated inflammation when used in conjunction with other cytokines.

Example 4

Production and Purification of Antibodies

BALB/C mice were first primed with 0.5 ml of pristane (2,4,6,10 tetramethylpentadecane, Aldrich, Milwaukee, Wis.). Two weeks later $1 \times 10^6$ mouse hybridomas in PBS were injected intraperitoneally into the mouse. Approximately two to five weeks later ascites fluid was removed from the mouse, and centrifuged to remove cells and particulate matter.

Five milliliters of ascites fluid was applied to a 3 ml column of protein A sepharose (Pharmacia, Piscataway, N.J.) diluted 1:4 with 0.1M ammonium sulfate, pH9. The column was washed with 10-20 column volumes of ammonium sulfate, pH9. Purified antibody was then eluted with 0.05M citrate, pH3.0, and neutralized with 1M NaOH.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A murine monoclonal antibody selected from the group consisting of HuCD40-M2 (ATCC HB 11459) and monoclonal antibodies that bind the same epitope bound by HuCD40-M2.

2. A murine monoclonal antibody produced by the murine hybridoma HuCD40-M2 (ATCC HB 11459).

3. A human monoclonal antibody according to claim 1.

4. A binding protein comprising a CD40-binding domain of an antibody according to claim 1, selected from the group consisting of a humanized monoclonal antibody, a single-chain Fv fragment, and a bivalent Fv fragment.

5. A humanized monoclonal antibody according to claim 4.

6. A CD40-binding domain of an antibody according to claim 2, selected from the group consisting of a humanized monoclonal antibody, a single-chain Fv fragment, and a bivalent Fv fragment.

* * * * *